(12) United States Patent
Castillo

(10) Patent No.: US 6,962,571 B2
(45) Date of Patent: *Nov. 8, 2005

(54) JOINT BRACE WITH MULTI-PLANAR PIVOTING ASSEMBLY AND INFINITELY ADJUSTABLE LIMB EXTENSION REGULATOR

(75) Inventor: James Castillo, Los Alamos, CA (US)

(73) Assignee: Asterisk.Asterisk, LLC, Foothill Ranch, CA (US)

(*) Notice: Subject to any disclaimer, the term of this patent is extended or adjusted under 35 U.S.C. 154(b) by 549 days.

This patent is subject to a terminal disclaimer.

(21) Appl. No.: 10/067,498

(22) Filed: Feb. 4, 2002

(65) Prior Publication Data

US 2002/0107463 A1 Aug. 8, 2002

Related U.S. Application Data

(63) Continuation-in-part of application No. 09/776,523, filed on Feb. 2, 2001.

(51) Int. Cl.$^7$ .................................................. A61F 5/00
(52) U.S. Cl. ........................................ 602/16; 602/26
(58) Field of Search .............................. 602/16, 26–27, 602/23, 5, 61; 128/878, 882

(56) References Cited

U.S. PATENT DOCUMENTS

| | | |
|---|---|---|
| 1,390,915 A | 9/1921 | Loth |
| 2,531,486 A | 11/1950 | Weber |
| 2,883,982 A | 4/1959 | Rainey |
| 3,030,634 A | 4/1962 | Bair |
| 3,099,448 A | 7/1963 | Salvo et al. |
| 3,387,305 A | 6/1968 | Shafer |
| 3,669,105 A | 6/1972 | Castiglia |
| 3,779,654 A | 12/1973 | Horne |
| 3,785,372 A | 1/1974 | Craig |
| 3,817,244 A | 6/1974 | Taylor |
| 3,900,898 A | 8/1975 | Kerman |
| 3,902,482 A | 9/1975 | Taylor |
| 3,928,872 A | 12/1975 | Johnson |
| 3,958,569 A | 5/1976 | Vosburgh |
| 4,136,404 A | 1/1979 | Lange |
| 4,169,467 A | 10/1979 | Rabischong et al. |
| 4,241,730 A | 12/1980 | Helfet |
| 4,271,831 A | 6/1981 | Deibert |
| 4,361,142 A | 11/1982 | Lewis et al. |
| 4,372,298 A | 2/1983 | Lerman |
| 4,381,768 A | 5/1983 | Ericksen et al. |
| D269,379 S | 6/1983 | Bledsoe |
| 4,407,276 A | 10/1983 | Bledsoe |
| 4,428,369 A | 1/1984 | Peckham et al. |
| 4,487,200 A | 12/1984 | Feanny et al. |
| 4,489,718 A | 12/1984 | Martin |
| 4,493,316 A | 1/1985 | Reed et al. |

(Continued)

FOREIGN PATENT DOCUMENTS

| | | |
|---|---|---|
| EP | 297766 A | 4/1989 |
| WO | 8404240 | 11/1984 |

Primary Examiner—Gregory L. Huson
Assistant Examiner—Fenn C. Mathew
(74) Attorney, Agent, or Firm—Stetina Brunda Garred & Brucker

(57) ABSTRACT

A brace for stabilizing a joint such as a knee disposed between a first and second limb structure. The brace includes upper and lower frame members, cuffs for encompassing a portion of each limb structure, and a uniting pivoting joint member. The joint member includes two opposing pivoting assemblies, with each including a forward and a rearward arm member each having upper and lower ends spherically-pivotally connected to the upper and lower frame members for enabling multiple angular relationships. The pivoting assembly can include a limb extension regulator, preferably a cable, extending between the rearward arm member and the upper frame member to permit infinitely adjustable extendability of the brace-bearing limb. Most preferably, a visible measurement scale is provided for precise extension distances.

13 Claims, 11 Drawing Sheets

U.S. PATENT DOCUMENTS

| | | | |
|---|---|---|---|
| 4,494,534 A | 1/1985 | Hutson | |
| 4,503,846 A | 3/1985 | Martin | |
| 4,523,585 A | 6/1985 | Lamb et al. | |
| 4,554,913 A | 11/1985 | Womack et al. | |
| D284,702 S | 7/1986 | Castillo | |
| 4,599,998 A | 7/1986 | Castillo | |
| 4,603,690 A | 8/1986 | Skeen | |
| 4,614,181 A | 9/1986 | Karlsson | |
| 4,620,532 A | 11/1986 | Houswerth | |
| 4,621,624 A | 11/1986 | Rayboy | |
| 4,628,916 A | 12/1986 | Lerman et al. | |
| 4,665,905 A | 5/1987 | Brown | |
| 4,681,097 A | 7/1987 | Pansier | |
| 4,697,583 A | 10/1987 | Mason et al. | |
| 4,699,129 A | 10/1987 | Aaserude et al. | |
| 4,715,363 A | 12/1987 | Detty | |
| 4,723,539 A | 2/1988 | Townsend | |
| 4,753,240 A | 6/1988 | Sparks | |
| D298,568 S | 11/1988 | Womack | |
| 4,791,916 A | 12/1988 | Paez | |
| 4,803,975 A | 2/1989 | Meyers | |
| 4,854,308 A | 8/1989 | Drillio | |
| 4,856,501 A | 8/1989 | Castillo et al. | |
| 4,886,054 A | 12/1989 | Castillo et al. | |
| 4,938,207 A | 7/1990 | Vargo | |
| 4,940,044 A | 7/1990 | Castillo | |
| 4,964,402 A | 10/1990 | Grim et al. | |
| 4,986,264 A | 1/1991 | Miller | |
| D318,736 S | 7/1991 | Castillo | |
| 5,063,916 A | 11/1991 | France et al. | |
| 5,121,742 A | 6/1992 | Engen | |
| 5,135,469 A | 8/1992 | Castillo | |
| 5,230,697 A | 7/1993 | Castillo et al. | |
| 5,267,946 A | 12/1993 | Singer et al. | |
| 5,288,287 A | 2/1994 | Castillo | |
| D346,028 S | 4/1994 | Lengyel | |
| 5,356,370 A * | 10/1994 | Fleming | 602/16 |
| D357,070 S | 4/1995 | Castillo | |
| 5,472,412 A * | 12/1995 | Knoth | 602/26 |
| 5,547,464 A | 8/1996 | Luttrell et al. | |
| 5,571,206 A | 11/1996 | Varn | |
| 6,001,075 A * | 12/1999 | Clemens et al. | 602/16 |
| 6,796,951 B2 * | 9/2004 | Freeman et al. | 602/16 |

* cited by examiner

JOINT BRACE WITH MULTI-PLANAR PIVOTING ASSEMBLY AND INFINITELY ADJUSTABLE LIMB EXTENSION REGULATOR

CROSS REFERENCE TO RELATED APPLICATIONS

This application is a continuation-in-part of U.S. patent application Ser. No. 09/776,523, filed Feb. 2, 2001.

STATEMENT RE: FEDERALLY SPONSORED RESEARCH/DEVELOPMENT

Not Applicable

BACKGROUND OF THE INVENTION

This invention relates in general to braces for joint support, and in particular to an exteriorly positionable anatomical brace having a pivoting joint assembly with multi planar hinging for accurate alignment of joined limb structures in relation to each other, and additionally having an infinitely-adjustable, cable-controlled limb extension regulator.

Both injury and disease can affect the health, well-being, and operability of various joints of the human body. Chief among such joints are the knee and elbow where disease such as osteo-arthritis can curtail normal activity or where an injury such as a sports-related abuse or impact can prevent or severely limit continued activity. One manner of treating such joint conditions and/or preventing or reducing the severity of sports related injuries is to fit the wearer with an appropriate brace whereby a pivotal support member is positioned adjacent the affected joint and held in place usually by cuffs situated around limb structure sites above and below the supported joint. As is apparent, the cuffs are responsible for stabilizing the support member and therefore must be well secured to their associated limbs. In addition to requiring proper limb structure embrace by cuffs, a joint brace also requires a joint pivoting assembly that supports, stabilizes, and protects the actual joint itself while pivotally joining the cuffs. Thus, in the knee joint for example, the joint pivoting assembly of the brace most beneficially should pivot in one bending or extension plane while also permitting multi planar motion such that the lower leg beneath the knee can be moved in a normal manner and the upper and lower leg structures can align with each other in a natural manner. Further, it many times is desirable to be able to precisely and infinitely limit or regulate the distance of the pivotal extension plane at the knee while allowing natural bendability and normal multi planar motion up to the controlled extension distance. Unfortunately, however, present braces generally are not able to offer multi-planar alignment capabilities or infinite extension control, thereby requiring a user to endure single-plane pivotability along with either a self-limit or pre-set limit of limb extendability. In view of such restrictions, it is apparent that a need is present for a joint brace that permits substantially natural limb movement in conjunction with limb extension control as indicated for particular limb care.

Consequently, a primary object of the present invention is to provide a joint brace having a joint assembly with multi planar hinging for accurate alignment of joined limb structures in relation to each other.

Another object of the present invention is to provide a joint brace having an infinitely-adjustable limb extension regulator for limiting limb extension as indicated for a particular user.

These and other objects of the present invention will become apparent throughout the description thereof which now follows.

BRIEF SUMMARY OF THE INVENTION

The present invention is an exteriorly positionable anatomical brace for stabilizing a uniting pivoting joint such as a knee joint disposed between a first and second limb structure of a living being. The brace comprises an upper frame member and a lower frame member joined together by a pivoting joint member, with each such frame member having secured thereon a respective cuff for encompassing a portion of each limb structure above and below the joint. Retention of the brace in place at the joint site is preferably accomplished with respective upper and lower securement members each wrapping around a respective limb structure in alignment with and not encompassed by the cuff. The pivoting joint member comprises two opposing pivoting assemblies each positionable on one side of the anatomical joint of a wearer to thus join the upper and lower frame members together. Each of these assemblies includes a forward arm member and a rearward arm member each having an upper end and a lower end, with these ends connected respectively to the upper frame member and the lower frame member. Specifically, the upper ends of each arm are individually mounted within a spherically-pivotal socket in connection with the upper frame member, while the lower ends of each arm likewise are individually mounted within a spherically-pivotal socket in connection with the lower frame member. As is apparent, these individual spherical mounts permit the selection of differing pivot ratios at a total of eight sites (four sites per lateral and per medial side) to thereby enable the upper and lower frame members to assume many different angular relationships with each other. Because of the availability of such a vast number of relationship combinations, the frame members of the brace becomes substantially self-aligning with each individual joint encounter among many wearers, thus accomplishing simulation of actual limb movement and angular interrelations thereof as natural individual limb-structure correlations are maintained.

As earlier noted, proper joint care many times requires limited or regulated limb extension, with such control emanating at the pivoting joint member. While prior art controls typically include inserts of a predetermined size for placement in the base path of upper and lower frame travel, the limb extension regulator of the present invention is a cable, preferably fabricated of braided metal strands, extending between each rearward arm member and the upper frame member. A cable-length adjuster, preferably externally accessible, is provided for infinitely adjusting the length of cable available between the arm member and frame member to thereby regulate extendability of the brace-bearing limb. Most preferably, a visible measurement scale is provided for each cable such that available cable length on each side of the joint is adjusted to be substantially identical. In addition to being infinitely length-adjustable, the cable additionally provides a modicum of elasticity such that cessation of limb travel produces a less dramatic limb impact, but, instead, a gentler limb-extension termination for the wearer. The brace here defined therefore substantially simulates natural joint behavior along with extension control as individually indicated.

BRIEF DESCRIPTION OF THE DRAWINGS

An illustrative and presently preferred embodiment of the invention is shown in the accompanying drawings in which:

FIG. 7c is a top plan view along line 7c—7c of FIG. 7a;

FIG. 11 is an exploded perspective view of the joint assembly of FIG. 10a.

DETAILED DESCRIPTION OF THE INVENTION

Figure 1:
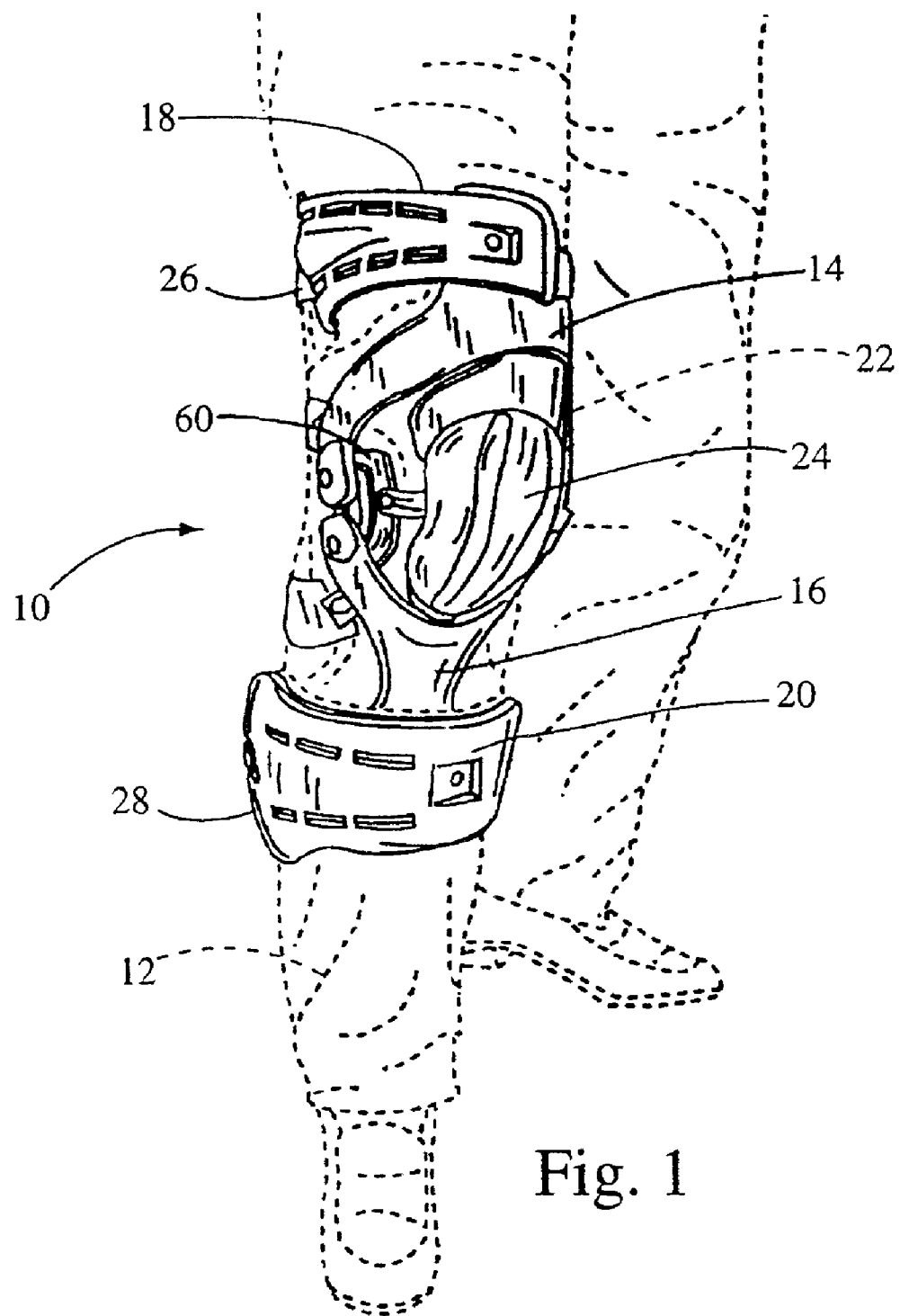
FIG. 1 is a perspective lateral view of a knee brace with upper and lower cuffs of respective upper and lower frame members in place on a patient leg shown in phantom.
Figure 2:
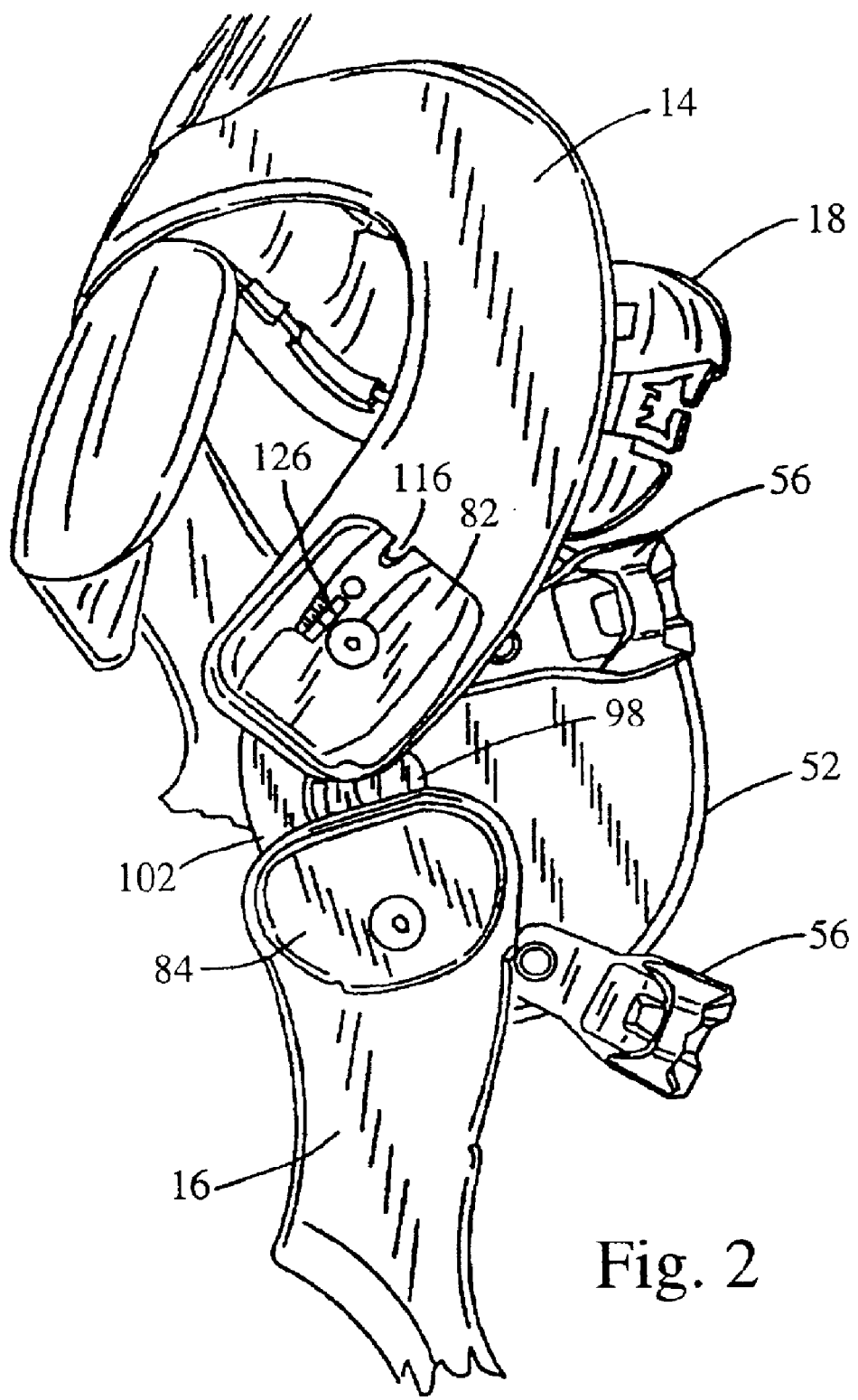
FIG. 2 is a perspective medial view of the knee brace of FIG. 1.
Figure 3:
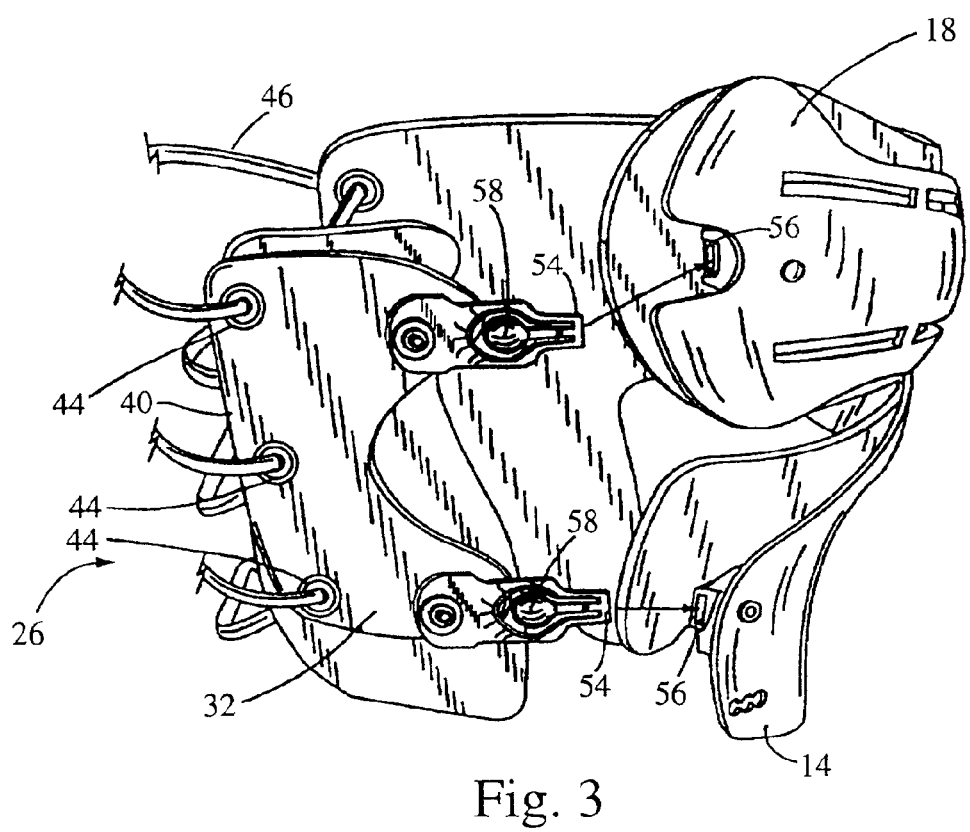
FIG. 3 is a lateral perspective view of the upper cuff and upper frame member only of FIG. 1 in disassociated relationship.
Figure 4:
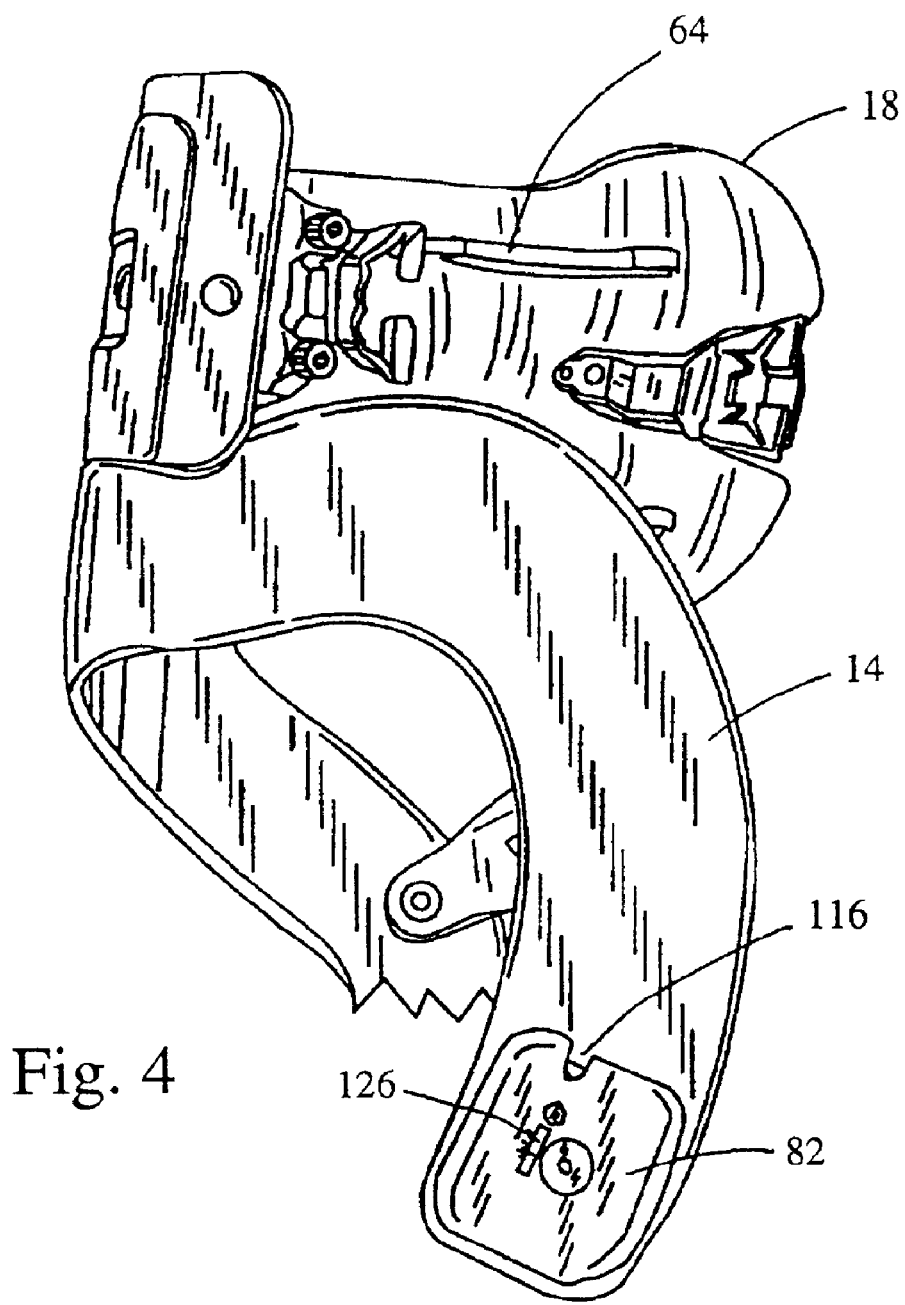
FIG. 4 is a medial perspective view of the upper cuff and upper frame member only of FIG. 3.
Figure 5:
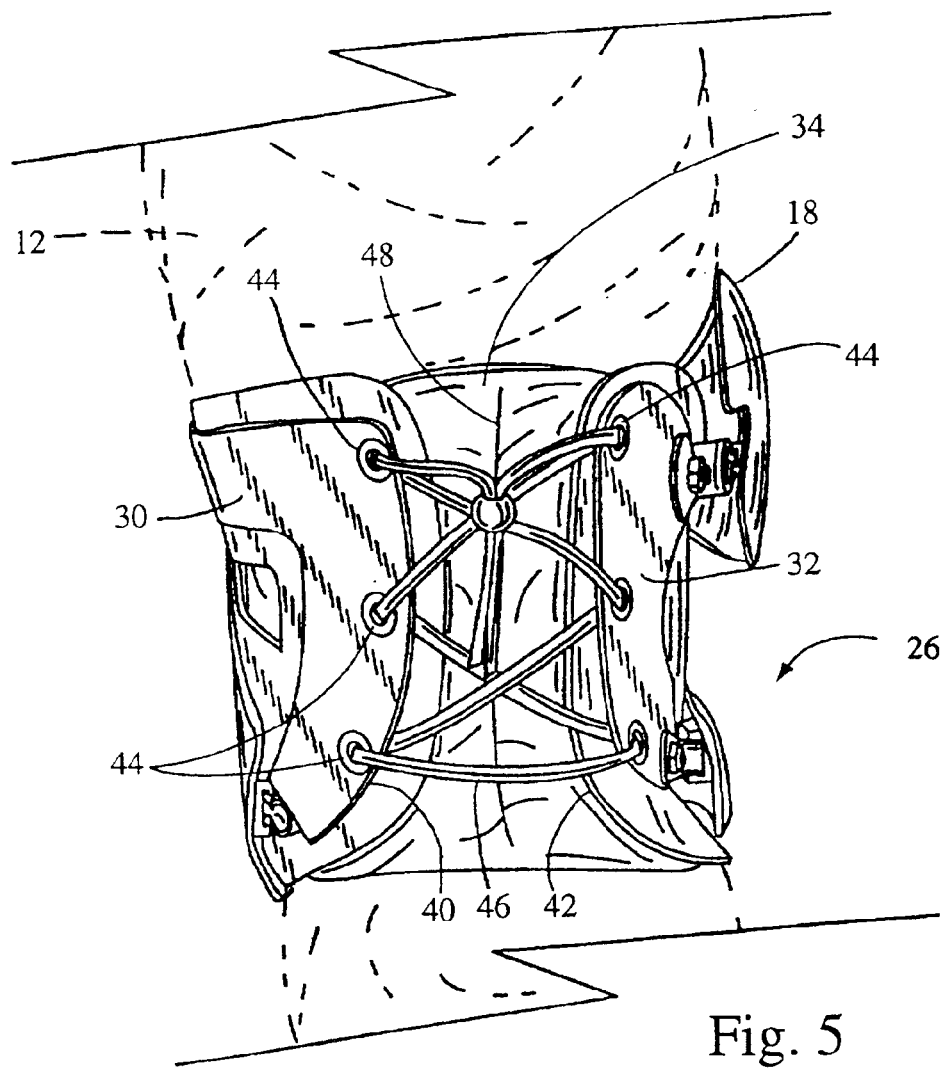
FIG. 5 is a rear perspective view of the upper cuff and upper frame member of FIG. 1 in place on a leg.

Referring first to FIGS. 1–5, a knee brace 10 is shown (FIG. 1) in place on a leg 12 of a human being. The brace 10 has an upper frame member 14 and a lower frame member 16, with each such frame member 14, 16 having secured thereon a respective cuff 18, 20 for disposition about the limb structures above and below the knee joint 22. Each cuff 18, 20 is an arcuate wall structure, which non-limitedly can be fabricated of a polymer plastic, for juxtapositioning with the respective limb structures as shown. A snap-in protective patella cup 24 can be included as shown for specific impact absorption that may occur at the patella of the knee joint 22.

The knee brace 10 is retained in place on the leg 12 with respective upper and lower securement members 26, 28 each respectively wrapping around an adjacent rear portion of the leg 12. While FIGS. 2–5 show only the upper securement member 26, it is to be understood that the following description thereof applies equally to the lower securement member 28. Thus, the securement member 26 includes a medial piece 30 and a lateral piece 32 each attached at outside edges thereof to an elastomeric central piece 34 disposed behind the medial and lateral pieces 30, 32. Respective inside edges 40, 42 of the medial and lateral pieces 30, 32 are provided with eyelets 44 through which is intertwined a length of non-elastomeric lace 46 in substantially the same manner as a shoe is laced to thereby permit the drawing of each inside edge 40, 42 toward each other. As would be recognized by the skilled artisan, hook-and-loop connectors (e.g. VELCRO) or other appropriate engagers can be employed in place of the length of lace 46. Finally, the elastomeric central piece 34 is secured along a generally central vertical length 48 thereof to a liner section (not shown) situated behind the central piece 34 to thereby permit elasticized movement of the medial and lateral pieces 30, 32.

The lateral piece 32 is releasably secured respectively to the upper cuff 18 and the upper frame member 14, and the medial piece 30 is releasably secured to the upper frame member 14 and the medial condyle 52, all by way of respective quick-release tab members 54 situated within respective slots 56. As shown, each tab member 54 is provided with a finger-receiving pressure button 58 which, when depressed, permits removal of the tab member 54 from the slot 56. In operation, the brace 10 is placed at the limb site of a user and positioned about the involved limb structures. Upon first placement of the brace 10, the lace 46 is tightened to appropriate tightness while the central piece 34 increases surface area on the leg 12 to disperse pressure and prevent pull from the leg 12 such that the cuff 18 is properly maintained in place. Once such lacing is accomplished the first time, re-lacing is not required during brace use. Specifically, when a user wishes to remove the brace, the user simply presses inwardly on the pressure buttons 58 of only laterally, or, preferably, only medially, situated tab members 54 to release these tab members 54 from their respective slots 56 and remove the brace 10 from the leg 12. It is important to note that the above-described tab-member release does not require increased tension on the leg and therefore is both safe and comfortable. Subsequent re-positioning of the brace 10 merely requires placement thereof as previously situated and re-connection of the earlier disengaged tab members 54 into respective slots 56. This re-connection requires no contact with, or re-adjustment of, the lace 46 or the central piece 34, and thereby assures proper brace placement without awkward, and very possibly incorrect, orientation of the brace 10. Because the medial connection involves connection to the medial condyle 52 which is, of course, at the hinge point of the upper and lower frame members 14, 16, a closer positioning of the securement member 26 to the body joint is permitted, thereby improving joint support. While a lateral condyle 60 does not bear a connector member, it is to be understood that such construction could be provided if desired.

Figure 6:
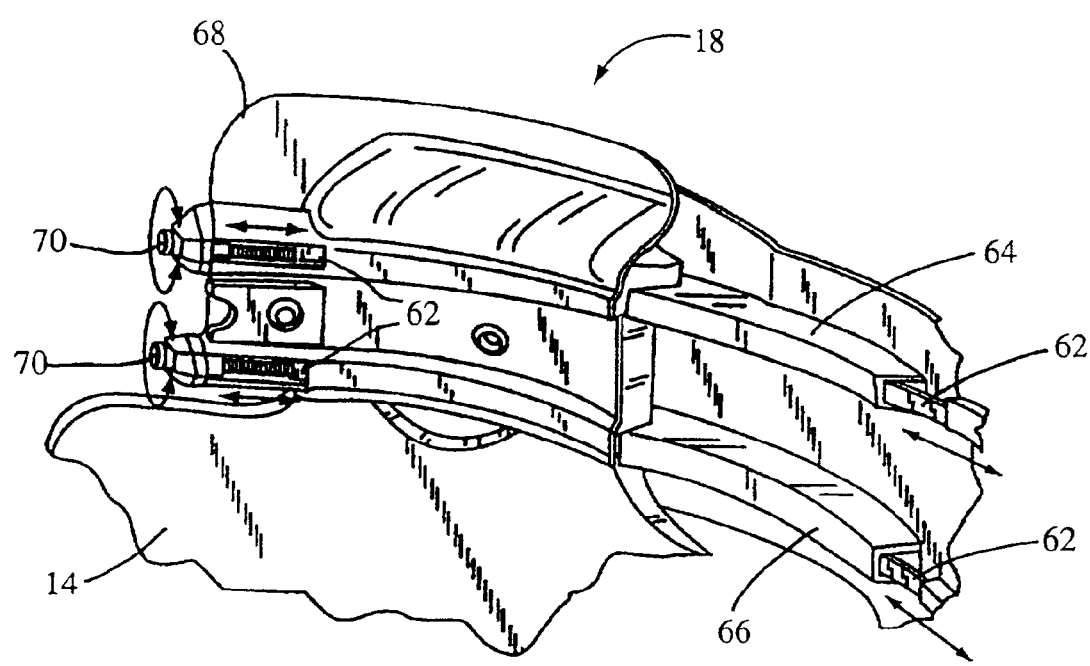
FIG. 6 is an interior perspective view of a portion of the upper cuff of FIG. 1.
Figure 7A:
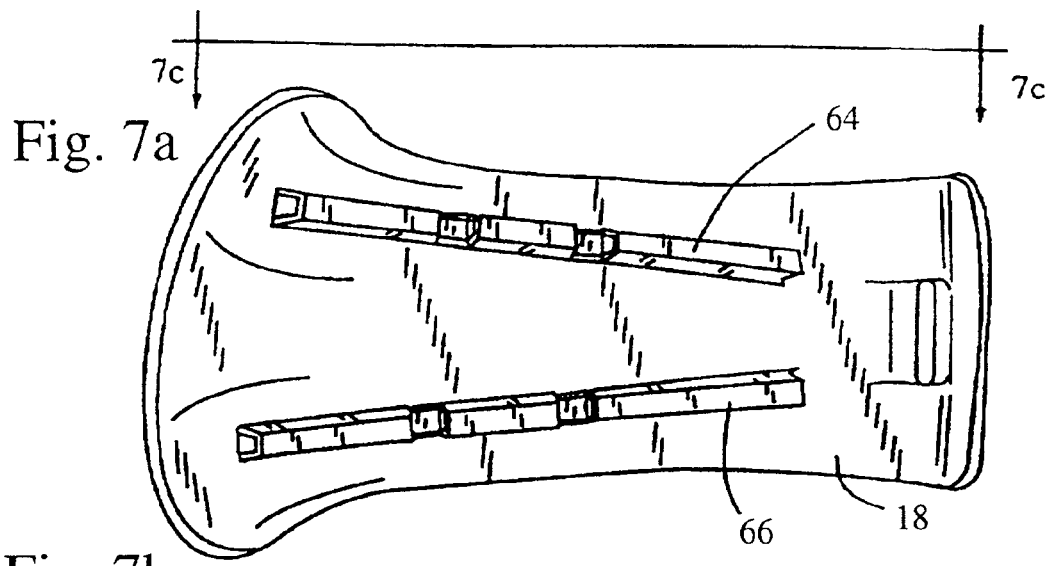
FIG. 7a is an interior side elevation view of the upper cuff of FIG. 4.
Figure 7B:
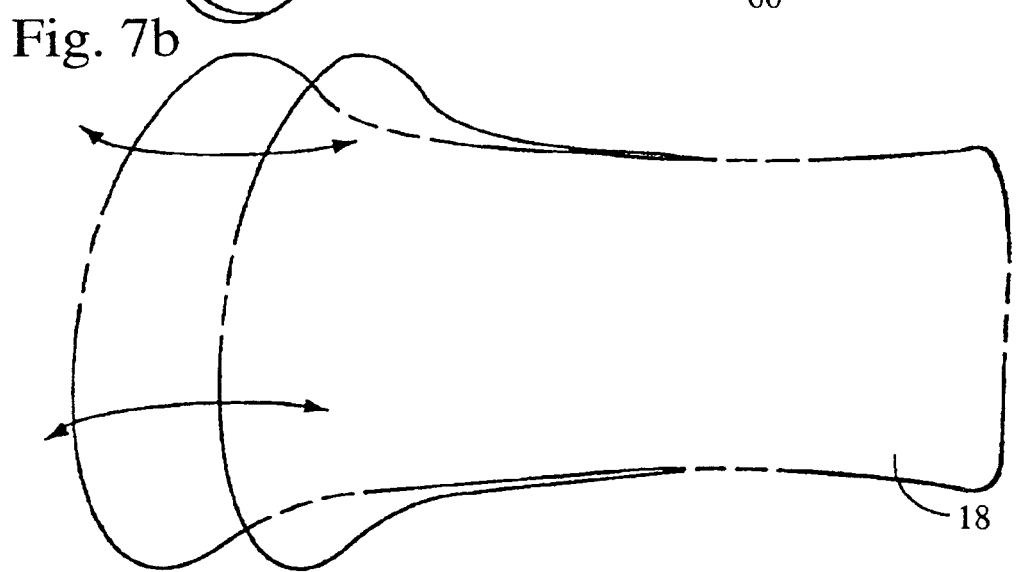
FIG. 7b is a schematic interior side elevation view of the cuff of FIG. 7a showing tensioning thereof.
Figure 7C:
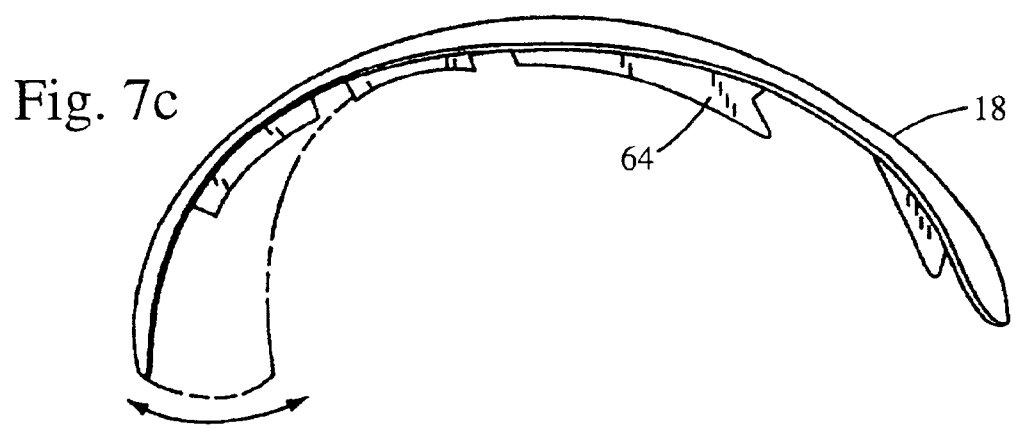
Figure 8:
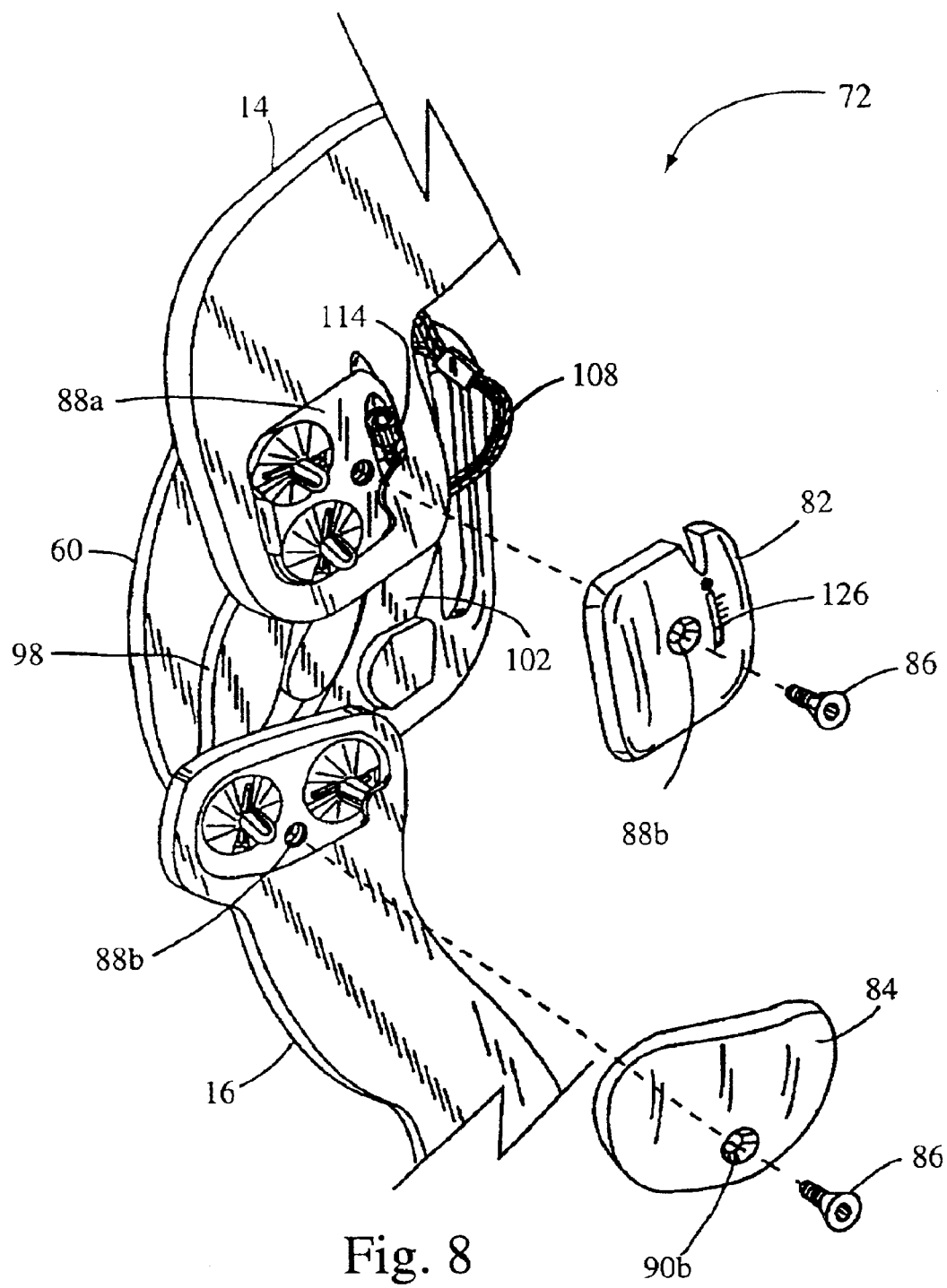
FIG. 8 is an inner perspective view of the joint assembly and respective portions of joined upper and lower frame members of FIG. 1.
Figure 9:
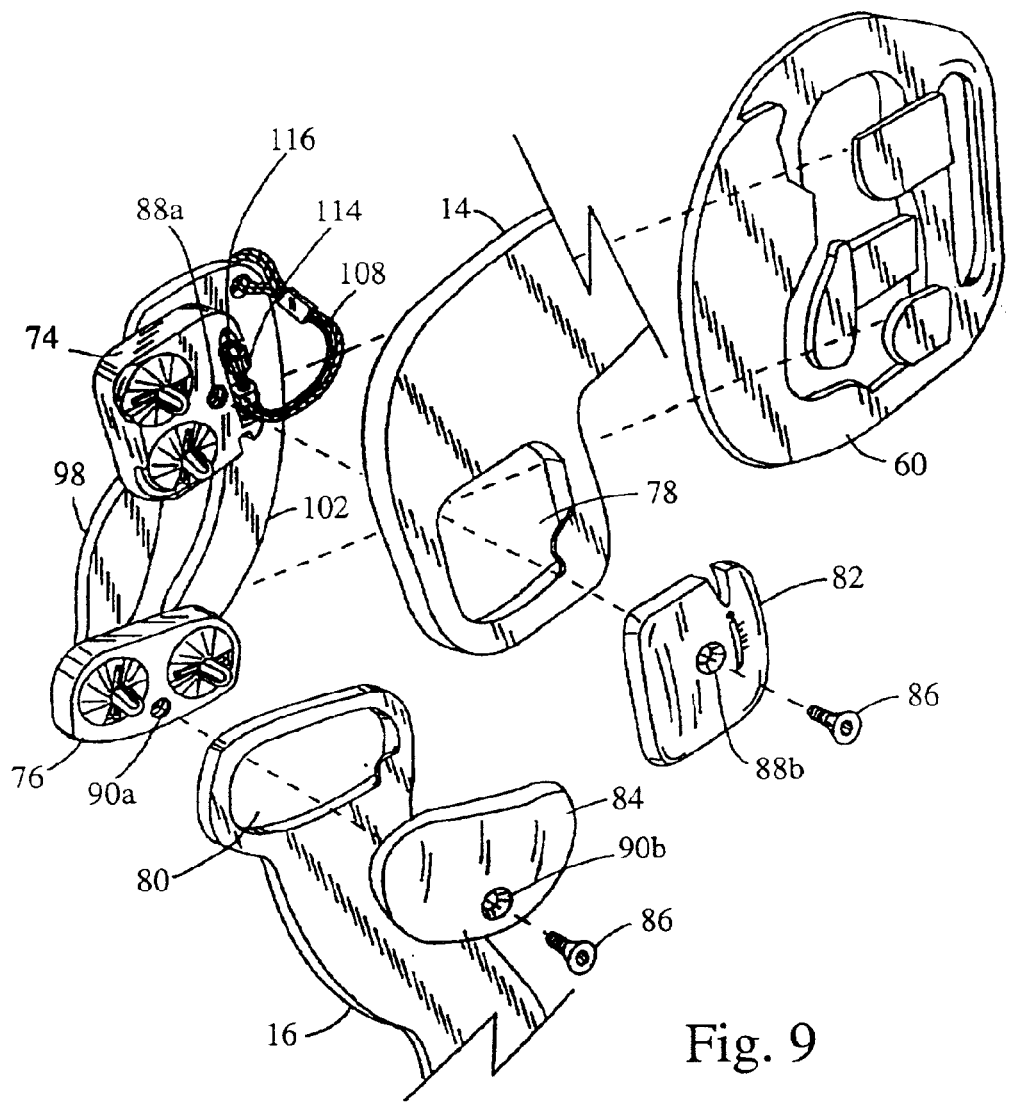
FIG. 9 is an exploded perspective view of the joint assembly and frame members of FIG. 8.
Figures 10A, 10B:
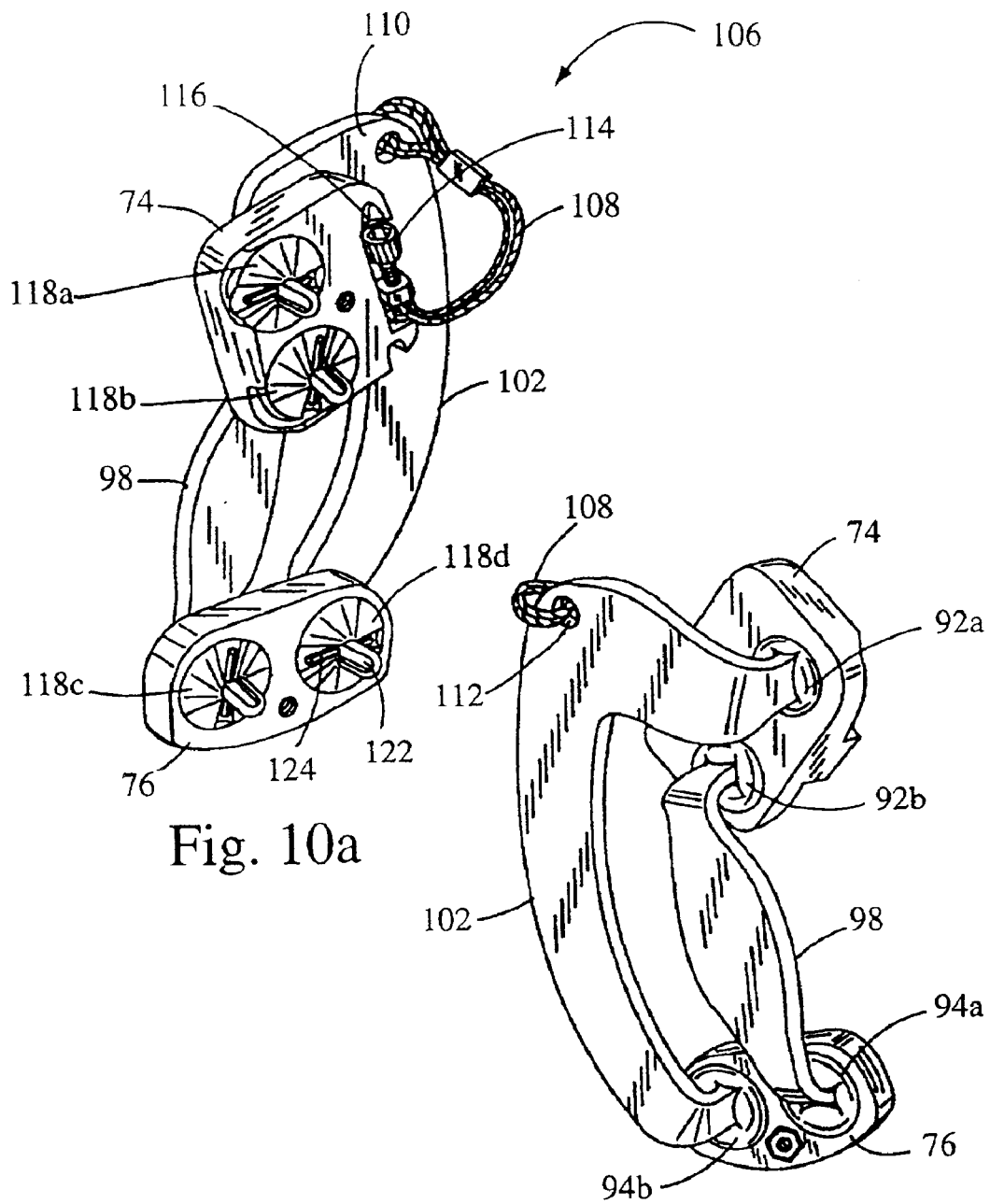
FIGS. 10a and 10b are perspective views of the inner and outer sides of the joint assembly of FIG. 8.
Figure 11:
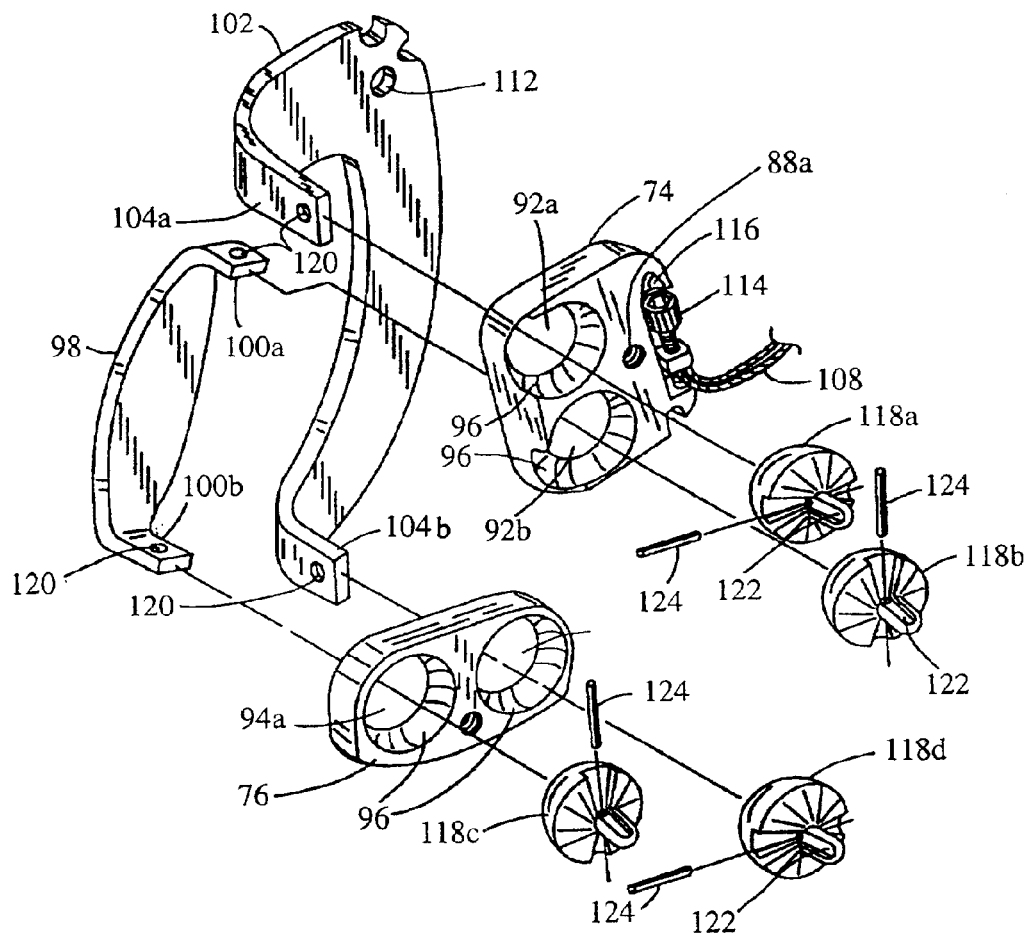

Construction of the cuffs 18, 20 is illustrated in FIGS. 6–7c. Both the upper cuff 18 and lower cuff 20 are substantially identical in construction except for overall size since, of course, the lower cuff 20 encompasses a smaller-diameter limb portion below the knee joint 22. As shown particularly in FIGS. 6 and 7a with respect to the upper cuff 18, whose following description also applies to the lower cuff 20, the cuff 18 has two tensioning strip members 62, integral therewith and disposed within respective non-continuous sleeves 64, 66 that are structurally a part of the cuff 18 and that converge toward each other medially. Each strip member 62, which preferably is fabricated of titanium, stainless steel, or similar material possessing similar tensioning properties, continues medially into a cuff mount 68 that functions to secure the cuff 18 to the upper frame member 14. Finally, a respective exteriorly-accessible threaded screw 70 extends into each strip member 62 for adjusting tension in each strip member 62 and simultaneously adjusting the arc defined by the upper cuff 18. Thus, clockwise turning of the screw 70 incrementally draws the lateral end of the strip member 62 medially for arcuately tightening the cuff 18, while counter clockwise turning of the screw 70 incrementally releases the lateral end of the strip member 62 for arcuately loosening the cuff 18. Operationally, the brace 10 is fitted to a patient by encompassing the cuffs about the respective limb structures above and below the knee joint 22 as seen in FIG. 1. Once the upper cuff 18 is situated about the limb structure, the screws 70 are threadingly advanced to thereby cause movement of the lateral end of the cuff 18, as illustrated in FIGS. 7b and 7c, against the limb structure as the strip members 62 are forced to bend toward the encompassed limb structure. Continued screw advancement increases tightening of the cuff 18 against the encompassed limb structure to thereby accomplish superior anchoring of the brace 10 and consequent stabilization of the knee joint 22. As earlier noted, the lower cuff 20 is constructed in the same manner as the upper cuff 18 and therefore encompasses and embraces the limb structure below the knee joint 22 in like fashion.

Referring to FIGS. 8–11, the pivoting assembly 72 uniting the upper and lower frame members 14, 16 is illustrated. The assembly 72 includes an upper housing 74 and a lower housing 76 that fit, respectively, into a complementarity shaped opening 78 of the upper frame member 14 and a complementarity shaped opening 80 of the lower frame member 16. Once so positioned, respective caps 82, 84 are held in place with conventional set screws 86 passing respectively through apertures 88a, 88b and 90a, 90b. Those skilled in the art however will recognize that the housings 74 and 76 can be formed unitary with the frame members 14 and 16. The lateral condyle 60 resides between the assembly 72 and the knee joint 22. Both the upper and lower housings 74, 76 have two respective openings 92a, 92b and 94a, 94b each having respective sidewalls 96 shaped to nest a spherical shape. Disposed between two openings 92b, 94a of the housings 74, 76 is a forward arm member 98 having generally perpendicularly angled first and second ends 100a, 100b directable toward the openings 92b, 94a. In like manner, a rearward arm member 102 having generally perpendicularly angled first and second ends 104a, 104b is disposed between two openings 92a, 94b of the housings 74, 76 such that the ends 104a, 104b are directable toward the openings 92a, 94b. A cable assembly 106 includes a cable 108 extending from the upper housing 74 to an upper edge portion 110 through an aperture 112 of the rearward arm member 102, and is provided with a conventional set screw 114 at one end thereof for extending or shortening the length of the cable 108 disposed between the rearward arm member 102 and upper housing 74. Such length adjustment is accomplished with an Allen wrench inserted into the enterable channel 116 leading to the set screw 114. Because the upper housing 74 resides within the upper frame member 14, the cable 108 functions as a joint extension limiter to determine the travel distance of the upper frame member 14 from the joint and thus the pivotal distance of the upper and lower frame members 14, 16 in relation to each other. An opening 126 can be provided in the cap 82 such that the progressive placement of the cable 108 can be observed exteriorly and such placement can be made identical for both the lateral and medial sides. Two additional benefits are provided by the cable 108 in that, first, infinite pivot-distance adjustability, as opposed to prior-art pre-sized stop members, allows great flexibility in leg extension, and, second, the cable itself has a dampening, or minimal stretch, effect that results in a softer extension stop and a consequent reduced risk of joint trauma.

As earlier described, the sidewalls 96 of the openings 92a, 92b and 94a, 94b are shaped to nest spherical forms. As clearly illustrated in FIG. 11, spherical sockets 118a, 118b, 118c, 118d are disposed in these openings 92a, 92b and 94a, 94b in the constructed assembly 72, and each such socket accepts one respective perpendicularly angled end of forward and rearward arm members 98, 102. Each angled end 100a, 100b, 104a, 104b has an aperture 120 there through which mates with a transverse aperture 122 of each socket 118a, 118b, 118c, 118d such that respective pins 124 can pass through such mated apertures and retain the angled ends 100a, 100b, 104a, 104b within the sockets 118a, 118b, 118c, 118d. Because of the spherical interface between each socket 118a, 118b, 118c, 118d and each sidewall 96, multi planar movement of the upper and lower frame members 14, 16 in relation to each other can be accomplished. In particular, the different pivot points thus provided allow different pivot ratios as needed for both lateral and medial sides to thereby simulate actual knee joint movement. This is, of course, in contrast to parallel planar hinges as found in the prior art where the knee joint and limb structures of a user are forced to adapt to knee brace construction instead of the knee brace adapting to the needs of the user. The present knee brace 10, because of the multi planar and potentially differing pivot ratios and consequent multi planar movement capabilities of the lower frame member 16 in relation to the upper frame member 14, provides automatic tibia alignment and automatic anatomical changes over time by accommodating anatomical differences among users. These properties accomplish all-important positive three-point positioning at the quadriceps muscle, the gastrocnemius (calf) muscle, and the knee joint itself. In this manner, stabilization and support of a uniting pivoting joint occurs economically, through an "off-the-shelf" brace, and, simultaneously, most effectively through continual self-alignment capabilities combined with sound limb-structure stability.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. An exteriorly positionable anatomical brace for stabilizing a uniting pivoting joint disposed between a first limb structure and a second limb structure of a living being, the brace comprising:

a) an upper frame member and a lower frame member;

b) an upper cuff for encompassing a portion of the first limb structure and secured to the upper frame member, and a lower cuff for encompassing a portion of the second limb structure and secured to the lower frame member;

c) an upper securement member for securing the upper cuff to the first limb structure, and a lower securement member for securing the lower cuff to the second limb structure; and d) a pivoting joint member connecting the upper and lower frame members, said joint member comprising two opposing pivoting assemblies each respectively positionable on one side of the uniting pivoting joint, wherein each said pivoting assembly comprises:

i) two upper spherically-pivotal socket mounts disposed in the upper frame member;

ii) two lower spherically-pivotal socket mounts disposed in the lower frame member;

iii) a forward arm member having an upper end being pivotally retained in a forward one of the upper spherically-pivotal socket mounts and a lower end being pivotally retained in a forward one of the lower spherically-pivotal socket mounts; and iv) a rearward arm member having an upper end being pivotally retained in a rearward one of the upper spherically-pivotal socket mounts and a lower end being pivotally retained in a rearward one of the lower spherically-pivotal socket mounts.

2. An exteriorly positionable anatomical brace as claimed in claim 1 wherein the two upper spherically-pivotal socket mounts have pivot ratios differing from each other.

3. An exteriorly positionable anatomical brace as claimed in claim 1 wherein the two lower spherically-pivotal socket mounts have pivot ratios differing from each other.

4. An exteriorly positionable anatomical brace as claimed in claim 1 wherein each of the spherically-pivotal socket mounts has a pivot ratio different from all other socket mounts.

5. An exteriorly positionable anatomical brace for stabilizing a uniting pivoting joint disposed between a first limb structure and a second limb structure of a living being, the brace comprising:
   a) an upper frame member and a lower frame member;
   b) an upper cuff for encompassing a portion of the first limb structure and secured to the upper frame member, and a lower cuff for encompassing a portion of the second limb structure and secured to the lower frame member;
   c) an upper securement member for securing the upper cuff to the first limb structure, and a lower securement member for securing the lower cuff to the second limb structure; and
   d) a pivoting joint member connecting the upper and lower frame members, said joint member comprising two opposing pivoting assemblies each respectively positionable on one side of the uniting pivoting joint, wherein each said pivoting assembly comprises:
      i) two upper spherically-pivotal socket mounts disposed in the upper frame member;
      ii) two lower spherically-pivotal socket mounts disposed in the lower frame member;
      iii) a forward arm member having an upper end being pivotally retained in a forward one of the upper spherically-pivotal socket mounts and a lower end being pivotally retained in a forward one of the lower spherically-pivotal socket mounts; and
      iv) a rearward arm member having an upper end being pivotally retained in a rearward one of the upper spherically-pivotal socket mounts and a lower end being pivotally retained in a rearward one of the lower spherically-pivotal socket mounts; and
      v) a substantially infinitely adjustable limb extension regulator for demarcating limb extension range.

6. An exteriorly positionable anatomical brace as claimed in claim 5 wherein the two upper spherically-pivotal socket mounts have pivot ratios differing from each other.

7. An exteriorly positionable anatomical brace as claimed in claim 5 wherein the two lower spherically-pivotal socket mounts have pivot ratios differing from each other.

8. An exteriorly positionable anatomical brace as claimed in claim 5 wherein each of the spherically-pivotal socket mounts has a pivot ratio different from all other socket mounts.

9. An exteriorly positionable anatomical brace as claimed in claim 5 wherein the limb extension regulator is an expanse of a length of cable extending between the rearward arm member and the upper frame member.

10. An exteriorly positionable anatomical brace as claimed in claim 9 wherein the length of cable is fabricated of braided metal strands.

11. An exteriorly positionable anatomical brace as claimed in claim 9 additionally comprising an exteriorly accessible controller for lengthening or shortening the length of cable extending between the rearward arm member and the upper frame member, thereby regulating limb extension distance.

12. An exteriorly positionable anatomical brace as claimed in claim 11 wherein the exteriorly accessible controller is a threadably-engaged screw shaft distally attached to the length of cable, said shaft being tool-accessible for rotation and resulting lengthening or shortening of the length of cable.

13. An exteriorly positionable anatomical brace as claimed in claim 11 additionally comprising an externally visible measurement scale for the length of cable such that respective lengths of cable extending between the rearward arm member and the upper frame member of each opposing pivoting assembly of the pivoting joint member can be made equal.

* * * * *